United States Patent [19]

Sneider

[11] 4,318,405
[45] Mar. 9, 1982

[54] TAMPON AND DRUG DELIVERY DEVICE

[76] Inventor: Vincent R. Sneider, 3422 Hallcrest Dr., N.E., Atlanta, Ga. 30319

[21] Appl. No.: 171,845

[22] Filed: Jul. 24, 1980

[51] Int. Cl.³ .............................................. A61F 15/00
[52] U.S. Cl. ..................................... 128/263; 128/270
[58] Field of Search ......................... 128/263, 270, 285

[56] References Cited

U.S. PATENT DOCUMENTS

| | | | |
|---|---|---|---|
| 2,509,241 | 5/1950 | Mende | 128/270 |
| 2,739,593 | 3/1956 | McLaughlin | 128/263 |
| 2,829,646 | 4/1958 | Kurkjian | 128/263 |
| 2,832,342 | 4/1958 | Wingenroth | 128/263 |
| 3,515,138 | 6/1970 | Hochstrasser et al. | 128/270 |
| 3,731,682 | 5/1973 | Fielding | |
| 3,884,233 | 5/1975 | Summey | 128/270 |
| 3,902,493 | 9/1975 | Baler et al. | 128/270 |
| 3,916,898 | 11/1975 | Robinson | 128/270 |
| 3,918,452 | 11/1975 | Cornfeld | 128/263 |
| 3,921,636 | 11/1975 | Zaffaroni | 128/270 |
| 4,186,742 | 2/1980 | Donald | 128/270 |

*Primary Examiner*—C. Fred Rosenbaum
*Attorney, Agent, or Firm*—Ralph R. Roberts

[57] ABSTRACT

A tampon and drug delivery device is disclosed and includes a generally cylindrical inserter tube defining a cartridge within which a tampon is slidably received for ejection through one end of the cartridge. A generally hollow cylindrical plunger member is slidably received within an opposite end of the cartridge for ejecting the tampon therefrom. A capsule of disintegrable material is partially embedded in and movably held by the tampon for delivery into a vaginal cavity, or the like, by ejection from the cartridge. The cartridge has a plurality of slots to permit prewetting of the tampon prior to insertion into the vaginal cavity.

9 Claims, 5 Drawing Figures

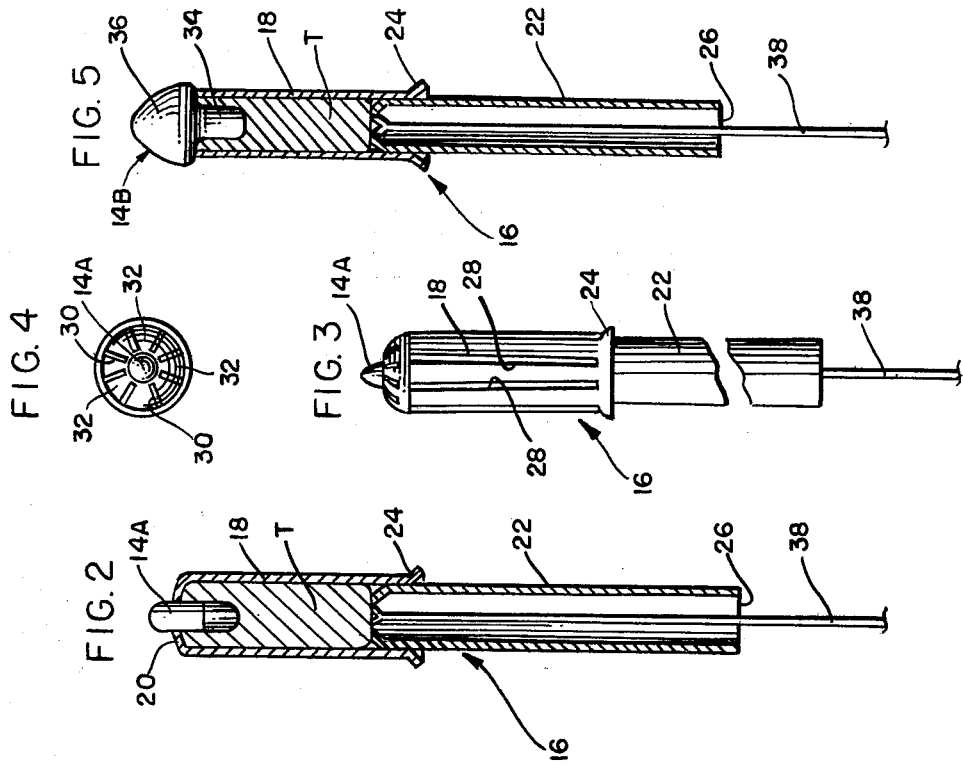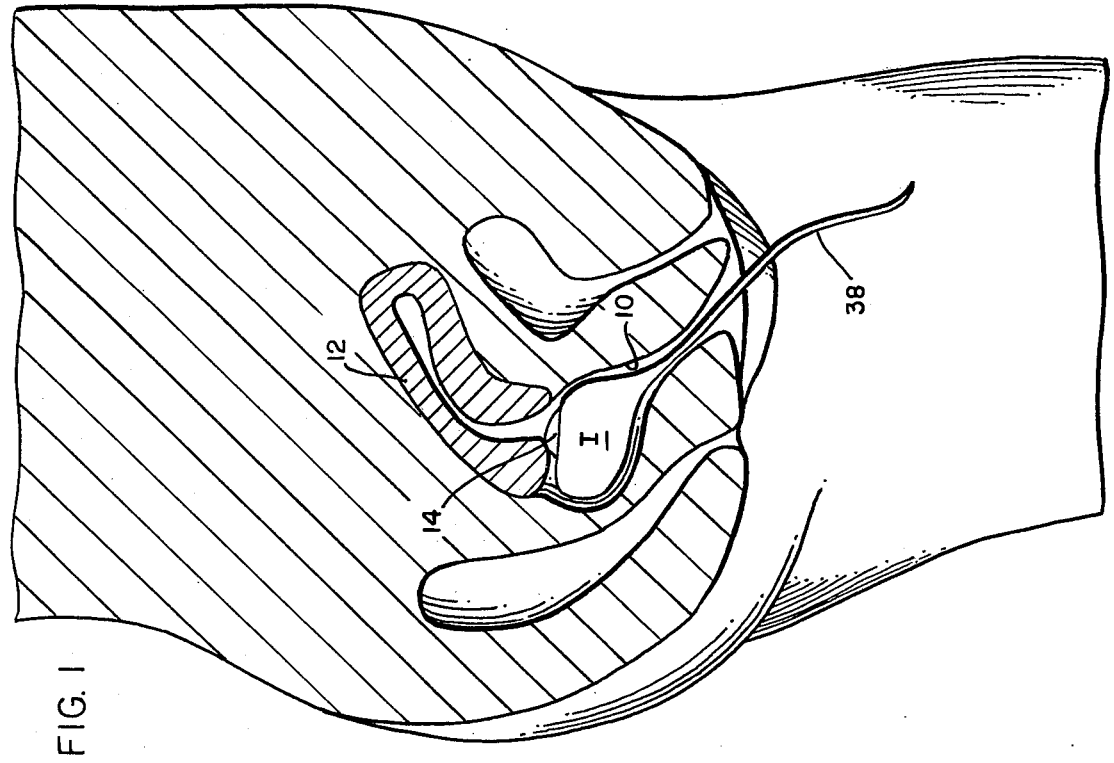

TAMPON AND DRUG DELIVERY DEVICE

BACKGROUND OF THE INVENTION

The present invention relates to a tampon and drug delivery device or combination, and particularly to a tampon in a form which carries a medicament into vaginal cavities or the like.

Medicated vaginal tampons and tampon and suppository combinations are known for delivering medicaments or drugs into vaginal cavities for various reasons such as contraception or hygienic purposes. In some instances, the tampon itself is impregnated with a particular solution or powered material. In other instances, it has become desirable to provide a means for delivering a drug into the vaginal cavity in the form of a capsule.

One of the problems with the utilization of capsule-like medicaments is that it is very difficult to properly locate and position the capsule for its intended purpose, because of the natural vaginal tendencies as a rejecting organ to flush or reject the capsule. The use of capsule-loaded tampons has been attempted, but, although the tampon is useful for initial insertion of the capsule, prior tampons utilized for these purposes could not properly locate and maintain the capsule in the desired position within the vaginal cavity.

U.S. Pat. No. 2,739,593 to McLaughlin, dated Mar. 27, 1956, and U.S. Pat. No. 3,884,233 to Summey, dated May 20, 1975, show medicated vaginal tampons or tampon and suppository combinations which are designed to deliver a medicament or suppository into the vaginal cavity. However, both of these patents exemplify the problems described above in properly inserting, locating and maintaining a capsule in a desired position within the vaginal cavity. In both of these patents, the tampon terminates appreciably short of the end of the cartridge therefor to define a socket for receiving the medicament or suppository. Not only does this unduly lengthen the overall dimensions of the devices, but once the medicament or suppository clears the socket defined by the tampon cartridge, there is no control whatsoever of properly locating the medicament or suppository within the vaginal cavity. With the natural vaginal rejecting tendencies, this is a serious problem with such devices heretofore available. In fact, Summey shows a device which includes a separate container and lid for the suppository utilized therein.

Another problem in utilizing tampons for delivering of the capsules is the fact that the absorbent nature of the tampon itself actually inhibits the dissolving or disintegration of the capsule containing the desired drug. More particularly, the particular drug, in capsule form, is mixed with a carrier material which is gradually broken down by body fluids. In using a tampon to deliver the capsule, the tampon itself has a tendency to absorb the body fluids rather than permitting the fluids to dissolve the capsule. Some capsules utilize carrier materials which dissolve in response to body temperature, but in many instances, it is undesirable to await this means to activate the capsule, rather the more effective activation means of utilizing body fluids.

The present invention is directed to fulfilling the aforesaid needs and solving the enumerated problems by providing a tampon and drug delivery device which has a more effective means for delivering a capsule-form drug into a vaginal cavity, or the like, and means for prewetting the capsule and provide a more effective means for activating the same.

SUMMARY OF THE INVENTION

An object, therefore, of the present invention is to provide a new and improved, novel tampon and drug delivery device of the character described.

In the exemplary embodiment of the invention, the tampon and drug delivery device includes a generally tubular inserter means, with a tampon slidably received within the inserter means for ejection through one end portion thereof. Ejecting means is slidably received within an opposite end portion of the inserter means for ejecting the tampon from said one end of the inserter means. A capsule of disintegrable material is at least partially embedded in and movably held by the tampon for delivery into a vaginal cavity, or the like, by ejection from the inserter means and held in proper position within the vaginal cavity by the tampon during activation of the capsule.

In one form of the invention, the capsule is embedded within the tampon generally centrally thereof at the end of the tampon adjacent said one end of the tubular inserter means. The one end of the inserter means closes over the peripheral edges of the tampon and is slotted to define generally triangularly shaped segments which surround and engage portions of the capsule protruding from the tampon.

In another form of the invention, the capsule is generally mushroom shaped with a stem portion embedded and held within the tampon, and a head portion overlapping the end of the tampon adjacent the forward end of the tubular inserter means.

As shown herein, the tubular inserter means is in the form of a cylindrical sheathing tube defining a hollow cartridge for receiving the tampon. The ejecting means which is slidably received within the inserter means is in the form of a hollow cylindrical plunger member. In this form, a withdrawal string is secured to the inner end of the tampon within the cartridge and extends through the hollow plunger member at the end thereof opposite the cartridge.

An important feature of the invention is the provision of aperture means in the inserter means to permit prewetting of the tampon prior to insertion into the vaginal cavity. In the exemplary embodiment of the invention shown herein, the aperture means comprises a plurality of slots extending lengthwise of the inserter means or cartridge and along a substantial length of the tampon. In this manner, the tampon and drug delivery device of the present invention can be submerged in a wetting solution, such as water, immediately prior to inserting the device into the vaginal cavity. The wetting solution is rapidly absorbed by the tampon and thereby preserves some of the body fluids for activating the capsule when deposited within the vaginal cavity.

It should be understood that the tampon and drug delivery device of the present invention has many functional applications, such as delivering capsule-form contraceptives for prevention of pregnancy and antibiodics for prevention or treating of venereal disease. In addition, such materials and beneficial agents as lubricants, deodorants, medication, natural secretion replacement, and other like applications for use in capsule form can be employed with the present invention where it is desirable to hold a beneficial agent or substance in proper position within the vaginal cavity.

Other objects, features and advantages of the invention will be apparent from the detailed description taken in connection with the accompanying drawings.

DESCRIPTION OF THE DRAWINGS

FIG. 1 is an anatomical diagram of a vaginal cavity, with a tampon and partially disintegrated capsule properly positioned therein by the device of the present invention;

FIG. 2 is a longitudinal central sectional view through an inserter and ejecting means, with one form of capsule carrying tampon of the present invention;

FIG. 3 is an elevational view of the device of FIG. 2, illustrating the slots in the inserter means for prewetting the tampon;

FIG. 4 is an end elevational view of the device of FIG. 2, illustrating the slotted triangularly shaped segments of the inserter means surrounding and engaging the capsule; and FIG. 5 is a longitudinal central sectional view through an inserter and ejecting means, with another form of capsule carrying tampon of the present invention.

DETAILED DESCRIPTION OF THE INVENTION

Referring to the drawings in greater detail, FIG. 1 is a female anatomical diagram illustrating a tampon T which has been inserted into a vaginal cavity 10. The tampon is expanded, and properly positioned adjacent the opening to uterus 12. A partially disintegrated capsule-form drug or medicament 14 is shown properly inserted and positioned by the expanded tampon. This view illustrates the desired functioning of the device of the present invention, after use, as now will be described.

Referring to FIG. 2, a tampon and drug delivery device in accordance with the present invention is generally designated 16. The device includes a generally tubular inserter means 18. The inserter means as shown is in the form of a cylindrical sheathing tube defining a cartridge for slidably receiving a tampon T for ejection through one end portion 20 of the cartridge.

Ejecting means 22, in the form of a hollow cylindrical plunger member, is slidably received within a flaired end 24 of cartridge 18 opposite end 20 of the cartridge. The ejecting plunger 22 engages the inner end of tampon T for ejecting the tampon from end 20 of cartridge 18. The flaired end 24 of cartridge 18 provides a finger grasping portion to facilitate ejection of the tampon by means of an individual's thumb engaging the outer end 26 of plunger member 22.

A capsule 14A of disintegrable material is partially embedded within and movably held by tampon T for delivery into vaginal cavity 10 (FIG. 1) by ejection from cartridge 18 after the cartridge is inserted into the vaginal cavity.

In the form of the invention shown in FIG. 2, capsule 14A is embedded and held within tampon T generally centrally thereof adjacent end 20 of cartridge 18. Normally, the compactness of the tampon would be sufficient for retaining and holding the capsule for proper insertion completely within the vaginal cavity as described in relation to FIG. 1. However, in certain circumstances, or with certain tampon material, it may be desirable to utilize a disintegrable adhering substance between the capsule and tampon to facilitate proper and precise positioning of the capsule within the vaginal cavity.

Referring to FIG. 3, an important feature of the invention is the provision of means on cartridge 18 for facilitating prewetting of tampon T prior to insertion into the vaginal cavity. More particularly, cartridge 18 is provided with aperture means in the form of a plurality of slots 28 through the sides thereof for prewetting the tampon. The slots preferably extend lengthwise of the cartridge along a substantial length of the tampon to insure complete wetting of the tampon. The tampon itself is fabricated of a compressed body of suitable soft, porous and absorbent material which expands appropriately within the vaginal cavity as shown in FIG. 1. This prewetting feature of the invention also is enhanced by the fact that the capsule is at least partially embedded within the tampon itself. In this manner, the embedded portion of the capsule is activated just as rapidly as the protruding portion which is activated primarily by body fluids. The combination of the prewetted tampon and the body fluids, promotes a rapid break-down of the carrier material for the particular drug embodied in the capsule. Thus, it can be seen that the embedding of the capsule within the tampon provides a dual function of insuring proper positioning of the capsule within the vaginal cavity as well as combining with the prewetting feature of the invention to insure rapid and uniform break-down of the capsule itself.

Referring to FIG. 4, it can be seen that the outer end of cartridge 18 closes over the peripheral edge of the tampon and is slotted, as at 30, to define generally triangularly shaped segments 32 which surround and engage the portions of capsule 14A which protrude from the tampon. These triangularly shaped segments also facilitate holding the capsule in proper position centrally embedded in the tampon.

Referring to FIG. 5, a modified form of capsule, generally designated 14B, is shown. Except for the elimination of the closed end 20 of cartridge 18, the tampon and associated components are identical to the device shown in FIGS. 2 and 3 and like numerals have been applied.

Capsule 14B shown in FIG. 5 is generally mushroom shaped with a stem portion 34 embedded and held within tampon T, similarly to the description of capsule 14A, above. Capsule 14B includes an enlarged, rounded head portion 36 which protrudes radially outwardly and overlaps both the end of tampon T and the open end of cartridge 18. Just as with the rounded end 20 and round capsule 14A in FIG. 2, the rounded head portion 36 of capsule 14B prevents any damage to the lining of the vaginal cavity and the uterus during insertion of the tampon and capsule thereinto.

With both forms shown in FIGS. 2 and 5, a withdrawal string 38 is secured at one end to the inner end of tampon T and extends completely through the opposite end of the hollow ejecting plunger member 22. After the tampon and capsule are properly inserted into the vaginal cavity, cartridge 28 and plunger member 22 may be discarded, leaving withdrawal string 38 for removing the tampon after a prescribed period of time.

It will be understood that the invention ma be embodied in other specific forms without departing from the spirit or central characteristics thereof. The present examples and embodiments, therefore, are to be considered in all respects as illustrative and not restrictive, and the invention is not to be limited to the details given herein.

I claim:

1. A tampon and drug delivery device, including:
   (a) a generally tubular inserter means having an entering end and a rear end;
   (b) a tampon slidably received and retained within said tubular inserter and adapted for discharge from and through the entering end;
   (c) ejecting means slidably received within the tubular inserter and at the rear end of said tubular inserter means, said ejecting means providing for the ejection of said tampon from the entering end of the inserter;
   (d) a capsule of disintegratable material at least partially embedded in and movably held in the entering end of said tampon for delivery into a vaginal cavity, or the like, by ejection from said inserter means, and
   (e) a capsule retaining means formed at and on the entering end of said tubular inserter means, said retaining means including an inwardly directed end portion having an aperture sized so as to engage and retain said capsule and with said entering end slotted to define and provide leaf segments biased to surround and engage that portion of the capsule protruding from said tampon.

2. The device of claim 1 wherein said capsule is embedded and held within said tampon generally centrally thereof at the entering end of the tampon adjacent said one end of said inserter means.

3. The device of claim 1 wherein said capsule is generally mushroom shaped with a stem portion embedded and held within said tampon, and a head portion overlapping the end of said tampon adjacent said one end of said inserter means.

4. The device of claim 1 wherein said inserter means includes aperture means to permit prewetting of said tampon prior to insertion into the vaginal cavity.

5. The device of claim 4 wherein said aperture means comprises a plurality of slots extending lengthwise of said inserter means and along a substantial length of said tampon.

6. The device of claim 1 wherein said capsule is substantially centrally located in the tampon end and said slots are arranged substantially radially so that the slots in said closed end portion are arranged to define generally triangular shaped segments.

7. The device of claim 6 wherein said capsule is embedded within said tampon generally centrally thereof at the end thereof adjacent said one end of said cartridge.

8. The device of claim 1 wherein the ejecting means includes a generally hollow cylindrical plunger member slidably, received within the rear end of said tubular inserter.

9. The device of claim 8, including a withdrawal string secured to the end of said tampon opposite said capsule and extending through the end of said hollow plunger member opposite said cartridge.

* * * * *